United States Patent [19]

Burri

[11] 4,355,823

[45] Oct. 26, 1982

[54] PRESSURE-SENSITIVE OR HEAT-SENSITIVE RECORDING MATERIAL

[75] Inventor: Peter Burri, Reinach, Switzerland

[73] Assignee: Ciba-Geigy Corporation, Ardsley, N.Y.

[21] Appl. No.: 171,635

[22] Filed: Jul. 24, 1980

Related U.S. Application Data

[63] Continuation of Ser. No. 15,979, Feb. 28, 1979, abandoned, which is a continuation of Ser. No. 842,855, Oct. 17, 1977, abandoned.

[30] Foreign Application Priority Data

Oct. 26, 1976 [LU] Luxembourg ........................... 76073

[51] Int. Cl.³ ........................ B41M 5/16; B41M 5/18; B41M 5/22
[52] U.S. Cl. ..................................... 282/27.5; 106/21; 260/315; 427/151; 428/320.4; 428/320.6; 428/320.8; 428/537; 428/913; 428/914
[58] Field of Search ................... 106/21, 31; 282/27.5; 427/150, 151; 428/307, 323, 411, 537, 913, 914, 320.4, 320.6, 320.8, 321.1; 260/315

[56] References Cited

U.S. PATENT DOCUMENTS

| | | | |
|---|---|---|---|
| 3,957,288 | 5/1976 | Lamahieu et al. | 282/27.5 |
| 3,958,815 | 5/1976 | Poot et al. | 282/27.5 |
| 3,995,088 | 11/1976 | Garner et al. | 428/323 |
| 4,054,718 | 10/1977 | Garner et al. | 428/454 |

*Primary Examiner*—Bruce H. Hess
*Attorney, Agent, or Firm*—Edward McC. Roberts

[57] ABSTRACT

The present invention relates to a pressure-sensitive or heat-sensitive recording material which contains as color former in its color-forming system at least one carbazolylmethane compound of the general formula

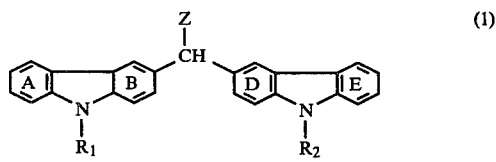

(1)

wherein each of $R_1$ and $R_2$ independently represents hydrogen, alkyl of not more 12 carbon atoms which is unsubstituted or substituted or alkenyl of not more than 12 carbon atoms, acyl of 1 to 12 carbon atoms, phenyl, benzyl, substituted phenyl or substituted benzyl, Z represents alkyl of 1 to 12 carbon atoms, alkenyl of not more than 12 carbon atoms, aryl, aralkyl, or represents a heterocyclic radical, and each of the rings A, B, D and E independently can be substituted or unsubstituted.

The carbazolylmethane compounds yield copies of improved color intensity and lightfastness.

13 Claims, No Drawings

PRESSURE-SENSITIVE OR HEAT-SENSITIVE RECORDING MATERIAL

This is a continuation of application Ser. No. 015,979 filed on Feb. 28, 1979, now abandoned, which is a continuation of Ser. No. 842,855 filed Oct. 17, 1977, now abandoned.

The present invention relates to a pressure-sensitive or heat-sensitive recording material which contains as colour former in its colour-forming system at least one carbazolylmethane compound of the general formula

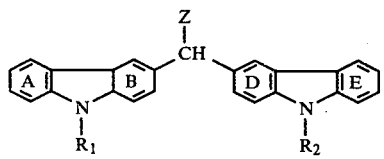

(1)

wherein each of $R_1$ and $R_2$ independently represents hydrogen, alkyl of not more 12 carbon atoms which is unsubstituted or substituted by halogen, hydroxyl, cyano or lower alkoxy, or alkenyl of not more than 12 carbon atoms, acyl of 1 to 12 carbon atoms, phenyl, benzyl, or phenyl or benzyl which are substituted by halogen, lower alkyl, lower alkoxy or nitro. Z represents alkyl of 1 to 12 carbon atoms, alkenyl of not more than 12 carbon atoms, aryl, aralkyl, or represents a heterocyclic radical, and each of the rings A, B, D and E independently can be substituted by cyano, nitro, halogen, lower alkyl, lower alkoxy or lower alkylcarbonyl.

In the definition of the radicals of the carbazolylmethane compounds, lower alkyl and lower alkoxy usually denote those groups or group components which contain 1 to 5, in particular 1 to 3, carbon atoms. Lower alkyl is for example methyl, ethyl, n-propyl, isopropyl, n-butyl, sec-butyl or amyl, and lower alkoxy is for example methoxy, ethoxy or isopropoxy. Halogen in connection with all the above substituents is for example fluorine, bromine or preferably chlorine.

Alkyl radicals represented by $R_1$ and $R_2$ can be straight-chain or branched. Examples of such alkyl radicals are: methyl, ethyl, n-propyl, isopropyl, n-butyl, sec-butyl, n-hexyl, n-octyl or n-dodecyl.

Substituted alkyl radicals represented by $R_1$ and $R_2$ are in particular cyanoalkyl, haloalkyl, hydroxyalkyl, alkoxyalkyl, each containing 2 to 4 carbon atoms, for example β-cyanoethyl, β-chloroethyl, β-hydroxyethyl, β-methoxyethyl or β-ethoxyethyl.

Alkenyl represented by $R_1$ and $R_2$ is for example allyl, 2-methallyl, 2-ethallyl, 2-butenyl or octenyl.

An acyl radical represented by $R_1$ and $R_2$ is in particular lower alkylcarbonyl, for example formyl, acetyl or propionyl, or benzoyl. Benzoyl can be substituted in the benzene ring by halogen, methyl or methoxy.

Preferred substituents in the benzyl and phenyl group of the radicals R are for example halogen atoms, methyl or methoxy groups. Examples of such araliphatic and aromatic radicals are: p-methylbenzyl, o- or p-chlorobenzyl, o- or p-tolyl, xylyl, o-, m- or p-chlorophenyl or o- or p-methoxyphenyl.

The substituents $R_1$ and $R_2$ are preferably alkyl of 1 to 12 carbon atoms, in particular alkyl of 1 to 5 carbon atoms, phenyl or benzyl.

As an alkyl or alkenyl radical, Z can have the same meanings as have been given for the radicals R, each of which is preferably substituted by an aryl radical, for example phenyl, to form an aralkyl or aralkenyl radical containing preferably 1 to 4 carbon atoms in the aliphatic portion, for example in the benzyl, piperonyl or styryl groups.

An aryl radical represented by Z can be phenyl, diphenyl or naphthyl.

These aromatic carbocyclic groups, and especially phenyl, can contain halogen, cyano, nitro, lower alkyl, lower alkoxy, methylenedioxy, di-lower alkylamino, N-phenyl-N-lower alkylamino, N,N-diphenylamino or acyl of 1 to 8 carbon atoms, whilst the benzene nuclei in the amino groups can be substituted by lower alkyl, lower alkoxy or halogen. Particularly preferred acyl radicals are alkanoyl radicals of 2 to 4 carbon atoms, such as acetyl or propionyl.

An aryl radical Z is preferably phenyl or phenyl which is substituted by halogen, methoxy, methyl, di-lower alkylamino, N-phenyl-N-lower alkylamino, N-lower alkoxyphenyl-N-lower alkylamino or N,N-diphenylamino. Examples of these aryl radicals are: phenyl, o-, m- or p-methylphenyl, o-, m- or p-methoxyphenyl, o-, m- or p-chlorophenyl, o-, m- or p-bromophenyl or o-, m- or p-fluorophenyl, 3,4-dimethoxyphenyl, 3,4-dichlorophenyl, 4-dimethylaminophenyl, 4-diethylaminophenyl, 4-(N-p-methoxyphenyl-N-methylamino)-phenyl, 4-(N-p-ethoxyphenyl-N-methylamino)-phenyl, 4-(N-phenyl-N-methylamino)-phenyl, 4-(N,N-diphenylamino)-phenyl, and naphthyl.

As a heterocyclic radical, Z represents advantageously a 5- or 6-membered heterocyclic ring of aromatic character which preferably contains oxygen, sulphur or nitrogen. Examples of such heterocyclic rings are: thienyl, furyl, pyrrolyl, pyrazolyl, pyrazolonyl, triazolyl, pyridyl, thiazinyl or exazinyl radicals. In this connection, Z can also represent a radical which is derived from polynuclear condensed heterocyclic rings which preferably contain a condensed benzene or naphthalene ring, and is for example an unsubstituted or substituted benzothiophene, indole, indazole, benzothiazole, benzotriazole, naphthotriazole, carbazole, quinoline, phenothiazine, or phenoxazine radical. These mononuclear or polynuclear heterocyclic radicals can contain the above mentioned substituents, in particular halogen atoms, hydroxyl, cyano, amino, nitro, alkyl of 1 to 8 carbon atoms, lower alkoxy, lower alkylcarbonyl, phenyl or benzyl.

Preferred heterocyclic radicals represented by Z are 3-carbazolyl, N-benzyl-3-carazolyl or N-lower alkyl-3-carbazolyl, for example N-methyl-3-carbazolyl, N-n-butyl-3-carbazolyl or, in particular, N-ethyl-3-carbazolyl. Further preferred examples of heterocyclic radicals Z are: 2-furyl, 2-thienyl, 4-pyridyl, 2-N-methylpyrrolyl, 3-indolyl, 2-lower alkyl-3-indolyl, 2-phenyl-3-indolyl, 1-acetyl-3-indolyl, 1-lower alkyl-2-methyl-indolyl, such as 1-ethyl-2-methylindolyl, 1-phenyl-3-methyl-5-pyrazolon-4-yl, 1-phenyl-3-methyl-5-amino-pyrazol-4-yl and 1-methyl-2,4-dioxoquinolinyl.

The rings A, B, D and E are preferably not further substituted or, if they do contain substituents, each independently is substituted in particular by halogen, lower alkyl or lower alkoxy, for example by chlorine, methyl or methoxy. Advantageously, each benzene ring can contain 1 or 2 substituents. The substituents of the rings A and E are preferably in the para-position to the nitrogen atom.

Carbazolylmethane compounds which are of practical importance have the general formula

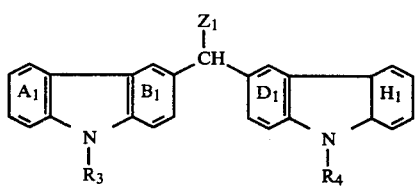

wherein each of $R_3$ and $R_4$ independently represents hydrogen, alkyl of not more than 12 carbon atoms which is unsubstituted or substituted by halogen, cyano or lower alkoxy; phenyl; or benzyl which is unsubstituted or substituted by halogen, lower alkyl or lower alkoxy, and $Z_1$ represents aryl or a heterocyclic radical and each of the rings $A_1$, $B_1$, $D_1$ and $E_1$ independently can be substituted by cyano, halogen, lower alkyl or lower alkoxy.

Preferred carbazolylmethane compounds of the formulae (1) and (2) above are those in which both carbazolyl radicals are identical.

Particularly interesting carbazolylmethane compounds are those of the general formula

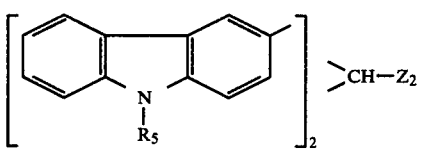

wherein $R_5$ represents alkyl of 1 to 12 carbon atoms, phenyl or benzyl, $Z_2$ represents an aryl radical selected from the group consisting of phenyl, diphenyl and naphthyl, and which can be substituted by halogen, nitro, lower alkyl, lower alkoxy or the amino group

in which each of $T_1$ and $T_2$ independently represents hydrogen, phenyl, lower alkoxyphenyl, lower alkyl or lower alkylcarbonyl, or $T_1$ and $T_2$ together with the nitrogen atom to which they are attached form a 5- or 6-membered, preferably saturated, heterocyclic radical, or $Z_2$ represents a heterocyclic radical selected from the group consisting of furyl, thienyl, pyrrolyl, pyrazolyl, aminopyrazolyl, pyrazolonyl, pyridyl, pyridonyl, thiazinyl, oxazinyl, indolyl, indazolyl, benzothienyl, benzothiazolyl, benzotriazolyl, naphthotriazolyl, quinolyl, quinololyl, carbazolyl, phenothiazinyl or phenoxazinyl, and the mononuclear or polynuclear heterocyclic radicals can be substituted by halogen, hydroxyl, cyano, nitro, alkyl of 1 to 8 carbon atoms, lower alkoxy, benzyl or phenyl.

A heterocyclic radical represented by $T_1$ and $T_2$ together with the nitrogen atom to which they are attached is for example pyrrolidino, piperidino, pipecolino, morpholino, thiomorpholino or piperazino.

Particularly useful carbazolylmethane compounds of the formulae (1) to (3) above are those bis-carbazolylmethane compounds as defined under (A) and (B) below:

A. Bis-carbazolylmethane compounds of the general formula

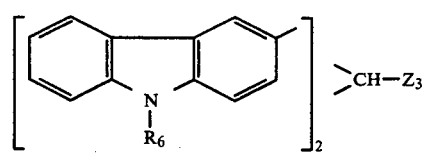

wherein $R_6$ represents alkyl of 1 to 8 carbon atoms or benzyl, and $Z_3$ represents phenyl or phenyl which is substituted by halogen, lower alkyl, lower alkoxy or the amino group

in which $T_3$ represents lower alkyl, phenyl or lower alkoxyphenyl, and $T_4$ represents hydrogen or lower alkyl.

Particularly preferred compounds of the formula (4) above are those in which $Z_3$ represents phenyl, halophenyl, methylphenyl, methoxyphenyl, di-(lower alkyl)-aminophenyl, N-phenyl-N-lower alkylaminophenyl, N-methoxy-phenyl-N-lower alkylaminophenyl or N-ethoxyphenyl-N-lower alkylaminophenyl.

B. Bis-carbazolylmethane compounds of the general formula

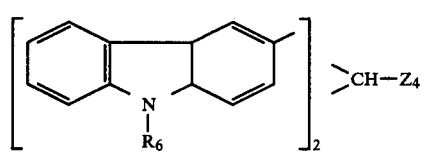

wherein $R_6$ is as defined in formula (4), and $Z_4$ represents furyl, thienyl, pyrazolonyl which can be substituted by lower alkyl and/or phenyl; pyridyl; pyrrolyl, indolyl or carbazolyl, each of which can be substituted by lower alkyl, lower alkylcarbonyl, phenyl or benzyl.

In this case, $R_6$ preferably represents alkyl of 1 to 8 carbon atoms, in particular lower alkyl or benzyl and $Z_4$ represents in particular carbazolyl or N-$C_1$-$C_8$alkyl-carbazolyl or N-benzyl-carbazolyl, especially N-lower alkylcarbazolyl, such as N-ethylcarbazolyl and N-butyl-carbazolyl.

The carbazolylmethane compounds of the formula (1) used in accordance with the invention are obtained by reacting, simultaneously or in succession, 1 mole of an aldehyde of the formula

Z—CHO    (6)

with 1 mole of each of the carbazole compounds of the formulae

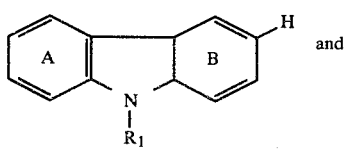

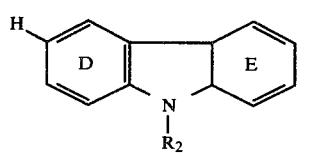

wherein A, B, D, E, R₁, R₂ and Z have the indicated meanings.

The reaction is advantageously carried out at a temperature between 20° and 130° C., preferably between 70° and 115° C. and in the presence of sulphuric acid, preferably 70 to 98% sulphuric acid. The reaction time depends on the temperature and is usually from 1 to 8 hours. To promote the solubility of the reagents and the product, it is possible to add lower aliphatic carboxylic acids or alcohols, for example acetic acid or isopropyl alcohol, to the reaction mixture, in which case the reaction temperature is between 20° C. and the reflux temperature of the mixture. In some cases it is advantageous to add urea in order to shorten the reaction time and to increase the yield. Instead of sulphuric acid, it is possible to use hydrochloric acid, zinc chloride, iron(III) chloride, aluminum chloride, polyphosphoric acid, phosphoroxy chloride, thionyl chloride or phosphorous pentoxide. It is often advantageous to use acetic anhydride both as reagent and as solvent. In this case, if for example Z represents an unsubstituted indolyl or carbazolyl radical at the nitrogen atom, an acetyl group can be introduced at the nitrogen atom during the reaction. The reaction can also be carried out in a water-insoluble solvent using for example phosphoroxy chloride or catalytic amounts of an organic sulphonic acid, for example p-toluenesulphonic acid.

The isolation of the end product of the formula (1) is effected in a manner which is known per se, for example by pouring the reaction mixture into ice-water, if appropriate while neutralising the acid with an alkaline compound, for example ammonia, an alkali metal hydroxide or an alkali metal carbonate, collecting the precipitate by filtration or evaporating off the water-insoluble solvent, and by washing and drying the product, as well as, if appropriate, by chromatography or recrystallisation of the product, which in certain cases can contain insignificant amounts of polycondensation products.

A preferred process for obtaining symmetrical compounds of the formula (1), wherein the carbazolyl radicals are identical, consists in reacting 1 mole of the aldehyde of the formula (6) with 2 moles of a carbazole compound of the formula (7) or (8).

The aldehydes of the formula (6) can be obtained in accordance with German Auslegeschrift No. 1,060,375, U.S. Pat. No. 2,558,285 or J. Org. Chem., Vol. 30, 3714–3718, (1965), by formylation of the compounds Z-H with dialkylformamides in the presence of an acid halide, and can also be used direct without being isolated.

The carbazolylmethane compounds of the formula (1) to (5) are normally colourless or faintly coloured. When these colour formers are brought into contact with an acid developer, i.e. an electron acceptor, they produce intense red to blue and green shades of excellent lightfastness. They are therefore also very useful when mixed with other known colour formers, for example 3,3-(bis-aminophenyl)-phthalides, 3,3-(bis-indolyl)-phthalides, 2,6-diaminofluoranes or spiropyranes, in order to give blue, navy blue, grey or black colourations.

The carbazolylmethane compounds of the formula (1) to (5) exhibit both on clay and on phenolic substrates an improved colour intensity and lightfastness. They are suitable in particular as slowly developing colour formers for use in a pressure-sensitive recording material, which can also be a copying material.

A pressure-sensitive material consists for example of at least one pair of sheets, which contain at least one colour former of the formulae (1) to (5) dissolved in an organic solvent, and a solid electron acceptor as developer. The colour former effects a coloured marking at those points where it comes into contact with the electron acceptor.

Typical examples of such developers are attapulgite clay, silton clay, silica, bentonite, halloysite, aluminium oxide, aluminium sulphate, aluminium phosphate, zinc chloride, kaolin or any clay or organic compound with acid reaction, for example unsubstituted or ring-substituted phenols, salicylic acid or esters of salicyclic acid and the metal salts thereof, or an acid polymeric material, for example a phenolic polymer, an alkylphenolacetylene resin, a maleic acid/rosin resin or a partially or completely hydrolysed polymer of maleic acid and styrene, ethylene, vinyl methyl ether or carboxypolymethylene. Preferred developers are attapulgite clay, silton clay or phenolformaldehyde resin. These electron acceptors are preferably applied in the form of a layer to the face of the receiver sheet. According to the invention, these developers and, in particular, attapulgite clay and silton clay, can be applied to paper not only in the customary alkaline to neutral range, for example at pH values between 7 and 12, preferably between 8 and 10, but also in the acid range, for example at pH values between 3 and 6.9, preferably between 4 and 6, whereby the carbazolylmethane compounds are distinguished in the acid range even by a higher rate and colour intensity during the colour development.

In order to prevent the colour formers contained in the pressure-sensitive recording material from becoming active too soon, they are usually separated from the electron acceptor substance. This can advantageously be accomplished by incorporating the color formers in foam-like, sponge-like or honeycomb-like structures. Preferably, however, the colour formers are enclosed in microcapsules, which as a rule can be ruptured by pressure.

When the capsules are ruptured by pressure, for example with a pencil, and the colour former solution is transferred in this manner to an adjacent sheet which is coated with an electron acceptor, a coloured area is produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example polyhalogenated diphenyl, such as trichlorophenyl or a mixture thereof with liquid paraffin; tricresyl phosphate, di-n-butyl phthalate, dioctyl phthalate, trichlorobenzene, nitrobezene, trichloroethyl phosphate, petroleum ether, hydrocarbon oils, such as paraffin, alkylated derivatives of naphthalene or diphenyl, terphenyls, partially hydrogenated terphenyl, or other chlorinated or hydrogenated condensed aromatic hydrocarbons. The capsule walls can be formed evenly around the droplets of the colour former solution by coacervation, and the encapsulating material can consist of gelatin and gum arabic, as described e.g. in U.S. Pat. No. 2,800,457. The capsules can be formed preferably also from an aminoplast or from modified aminoplasts by polycondensation, as described in British Pat. Nos. 989,264, 1,156,725, 1,301,052 and 1,355,124.

The microcapsules containing the colour formers of formula (1) can be used for the manufacture of a wide variety of known kinds of pressure-sensitive copying material. The various systems differ substantially from one another in the arrangement of the capsules, the colour reactants and the carrier material.

A preferred arrangement is that in which the encapsulated colour former is applied as a layer to the back of a transfer sheet and the electron acceptor substance as a layer to the face of a receiving sheet. However the components can also be used in the paper pulp.

Another arrangement of the constituents consists in the microcapsules which contain the colour former, and the developer, being in or on the same sheet, in the form of one or more individual sheets or being present in the paper pulp.

Such pressure-sensitive copying materials are described, for example, in U.S. Pat. Nos. 2,730,457, 2,932,582, 3,418,250, 3,418,656, 3,427,180 and 3,516,846. Further systems are described in British Pat. Nos. 1,042,596, 1,042,597, 1,042,598, 1,042,599, and 1,053,935. Microcapsules which contain the colour formers of formula (1) are suitable for each of these systems and for other pressure-sensitive systems.

The capsules are preferably secured to the carrier by means of a suitable adhesive. Since paper is the preferred carrier material, these adhesives are principally paper coating agents, for example gum arabic, polyvinyl alcohol, hydroxymethyl cellulose, casein, methyl cellulose or dextrin.

The term "paper" used herein comprises not only normal paper made from cellulose fibres, but also paper in which the cellulose fibres are replaced (partially or completely) by synthetic polymer fibres.

The carbazolylmethane compounds of the formulae (1) to (5) can also be used as colour formers in a thermoreactive recording material. This recording material contains normally at least one carrier, one colour former a solid electron acceptor and optionally also a binder. Thermoreactive recording systems comprise for example heat sensitive recording and copying materials and papers. These systems are used, for example, for recording information, e.g. in electronic computers, teleprinters or telewriters, and in measuring instruments. The image (mark) formation can also be effected manually with a heated pen. Laser beams can also be used to produce heat-induced marks. The thermoreactive recording material can be so composed that the colour former is dispersed or dissolved in one binder layer and the developer is dissolved or dispersed in the binder in a second layer. A second possibility consists in dispersing both the colour former and the developer in the binder in one paper. By means of heat the binder is softened at specific areas and the colour former comes into contact with the electron acceptor substance at those points where heat is applied and the desired colour develops at once.

The developers are the same electron-accepting substances as are used in pressure-sensitive papers. Examples of developers are the clays and phenolic resins already mentioned, or phenolic compounds, for example 4-tert. butylphenol, 4-phenylphenol, 4-hydroxydiphenyl oxide, $\alpha$-naphthol, $\beta$-naphthol, 4-hydroxymethyl benzoate, 4-hydroxyacetophenone, 2,2'-dihydroxydiphenyl, 4,4-isopropylidenediphenol, 4,4'-isopropylidene-bis-(2-methylphenyl), 4,4'-bis-(hydroxyphenyl)valeric acid, hydroquinone, pyrogallol, phloroglucinol, p-, m- and o-hydroxybenzoic acid, gallic acid, 1-hydroxy-2-naphthoic acid, as well as boric acid and aliphatic dicarboxylic acids, for example tartaric acid, oxalic acid, maleic acid, citric acid, citraconic acid or succinic acid.

Fusible, film-forming binders are preferably used for the manufacture of the thermoreactive recording material. These binders are normally water-soluble, whereas the colour formers and the developer are insoluble in water. The binder should be able to disperse and fix the colour former and the developer at room temperature.

By applying heat the binder softens or melts, so that the colour former comes in contact with the developer and a colour is able to form. Examples of binders which are soluble or at least swellable in water are hydrophilic polymers, for example polyvinyl alcohol, polyacrylic acid, hydroxyethyl cellulose, methyl cellulose, carboxymethyl cellulose, polyacrylic amide, polyvinyl pyrrolidone, gelatin and starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylmethacrylates, ethyl cellulose, nitrocellulose and polyvinyl carbazole. The preferred arrangement, however, is that in which the colour former and the developer are contained in one layer in a water-soluble binder.

The thermoreactive coatings can contain further additives. To improve the degree of whiteness, to facilitate the printing of papers, and to prevent the heated pen from sticking, the coatings can contain, for example, talc, $TiO_2$, $ZnO$ or $CaCO_3$ or also organic pigments, for example urea/formaldehyde polymers. In order to effect the colour formation only within a limited temperature range, it is possible to add substances such as urea, thiourea, acetanilide, phthalic anhydride or other appropriate fusible products which induce the simultaneous melting of the colour former and developer.

In the following Manufacturing Directions and Examples, the percentages are by weight unless otherwise indicated.

Manufacturing Directions

A. 7.5 g of p-dimethylaminobenzaldehyde and 20 g of N-ethylcarbazole are dissolved in 40 ml of isopropanol. Then 7 ml of 98% sulphuric acid are slowly added dropwise to the solution at 25° C. and 5 g of urea are added. The reaction mixture is heated to 75° C. and kept at this temperature for 4 hours. The reaction solution is subsequently poured, with stirring, into 400 ml of ice-water and adjusted to a pH value between 9 and 10 with a concentrated sodium hydroxide solution. The precipitate is then collected by filtration and recrystallised from acetone/methanol, affording 17 g of a colourless compound of the formula

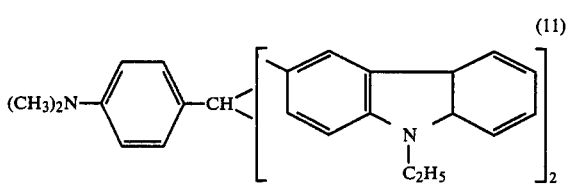
(11)

which melts at 149°–153° C. On silton clay this colour former slowly develops an intense, lightfast blue colour with λ max. at 595 nm.

B. 3 g of benzaldehyde and 12.3 g of N-ethylcarbazole are dissolved at 45° C. in 30 ml of isopropanol. Then 5.9 g of 98% sulphuric acid are added dropwise to the solution and 2.7 g of urea are subsequently added. The reaction mixture is heated to 75°–80° C. and kept at this temperature for 5 hours. When the condensation is complete, the solution is poured, with stirring, into a mixture of 50 ml of ethanol and 150 ml of ice-water and neutralised with a concentrated sodium hydroxide solution. The precipitate is collected by filtration and recrystallised from acetone/ethanol, affording 9.6 g of a colourless compound of the formula

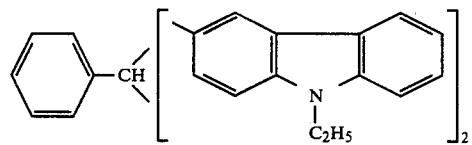
(12)

which melts at 204°–206° C. On silton clay, this colour former slowly develops an intense, lightfast green colour with λ max. at 638 and 460 nm.

C. 4.1 g of p-methoxybenzaldehyde and 12.3 g of N-ethylcarbazole are reacted in the same manner as described in (B) and the reaction product is isolated also as indicated therein, affording 6.9 g of a colourless compound of the formula

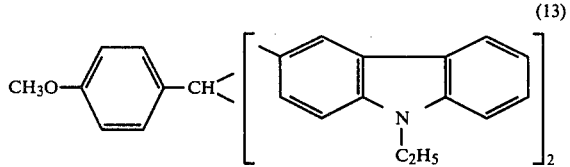
(13)

which melts at 121°–124° C. On silton clay this carbazolylmethane compound develops an intense lightfast blue colour of λ max. 610 and 520 nm.

D. 4.2 g of p-chlorobenzaldehyde and 12.3 g of N-ethylcarbazole are reacted in the same manner as described in (B) and the reaction product is isolated also as indicated therein, affording 11.1 g of a colourless compound of the formula

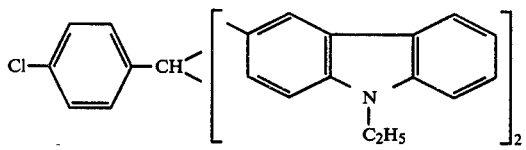
(14)

which melts at 128°–131° C. On silton clay this carbazolylmethane compound develops an intense lightfast green colour with λ max. at 655 and 460 nm.

E. 5 g of N-ethylcarbazole aldehyde and 8.4 g of N-ethylcarbazole are suspended in 25 ml of glacial acetic acid, 3.8 g of water and 1.5 g of urea. Then 2 ml of 37% hydrochloric acid are added dropwise at 60° C. to this suspension, the temperature is subsequently raised to 110° C., and the reaction mixture is kept for 1 hour thereat. After cooling, the precipitated product is collected by filtration and recrystallised from acetone/ethanol, affording 7.1 g of a colourless compound of the formula

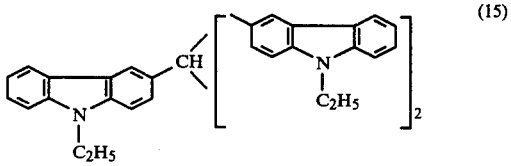
(15)

which melts at 205°–210° C. On silton clay this colour former slowly develops an intense light fast blue colour with λ max. at 615 nm.

F. 4.2 g of N-methylanilino-benzaldehyde and 7.8 g of N-ethylcarbazole are dissolved in 40 ml of ethylene chloride. To this solution are added 3.1 g of phosphoroxy chloride and the reaction mixture is stirred for 3 hours at 40° C. in a nitrogen atmosphere. The reaction mixture is then poured into water, neutralised with 30% ammonia solution and the ethylene chloride phase is separated. On pouring the ethylene chloride solution into methanol, the product precipitates in crystalline form. The precipitate is filtered off and dried in vacuo at 50° C., affording 4.3 g of a colourless compound of the formula

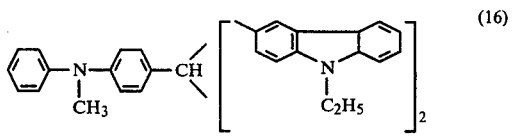
(16)

which melts at 165°–169° C. This colour former develops a lightfast blue colour on silton clay.

G. 4.8 of 4-[N-methyl-N-(p-methoxyphenyl)]-aminobenzaldehyde and 7.8 g of N-ethylcarbazole are dissolved in 30 ml of ethylene chloride. To this solution are added 6.1 g of phosphoroxy chloride and the mixture is stirred for 6 hours at 70° C. The reaction product is subsequently worked up as described in (F), affording 9.3 g of a colourless compound of the formula

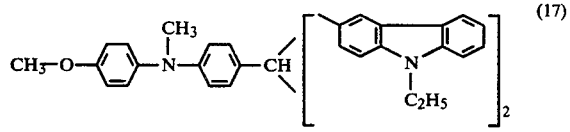 (17)

which melts at 145°–148° C. On silton clay this colour former slowly develops an intense lightfast blue colour with λ max. at 610 nm.

H. 4.7 g of 1-naphthaldehyde and 13.4 g of N-butylcarbazole are dissolved in 30 ml of ethylene chloride. To this solution are added 9.2 g of phosphoroxy chloride and the reaction mixture is stirred for 5 hours at 65° C. The reaction product is thereafter worked up as described in (F), affording 13 g of a colourless compound of the formula

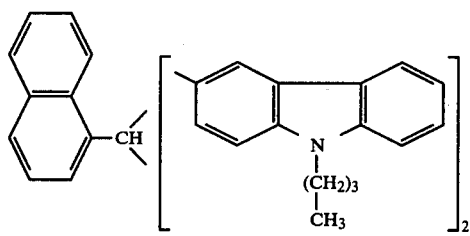 (18)

which melts at 179°–182° C. On silton clay this colour former develops an intense lightfast green colour with λ max. at 660 nm.

I. 2.15 g of benzaldehyde and 10.3 g of N-benzylcarbazole are dissolved in 30 ml of ethylene chloride. To this solution are added 6.1 g of phosphoroxy chloride and the reaction mixture is stirred for 5 hours at 54° C. The reaction product is thereafter worked up as described in (F), affording 9.2 g of a colourless compound of the formula

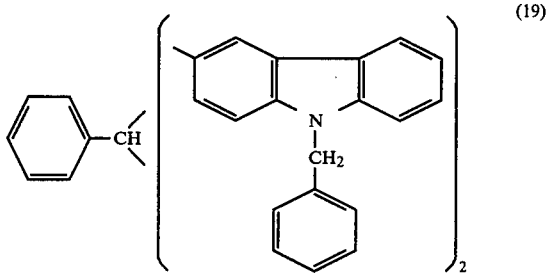 (19)

which melts at 118°–121° C. On silton clay this colour former slowly develops an intense lightfast green colour with λ max. at 635 nm.

J. 3.2 g of N-ethylcarbazole-3-aldehyde, 6.9 g of 3-chloro-N-ethylcarbazole and 0.9 g of urea are dissolved in 30 ml of glacial acetic acid. To this solution are slowly added 3 g of 98% sulphuric acid and the solution is stirred for 6 hours at 60° C.

The reaction mixture is subsequently poured into water and neutralised with a 30% ammonia solution. The precipitate which has formed is collected by filtration. The product is dissolved in hot acetone and the solution poured into methanol, giving 3 g of a colourless compound of the formula

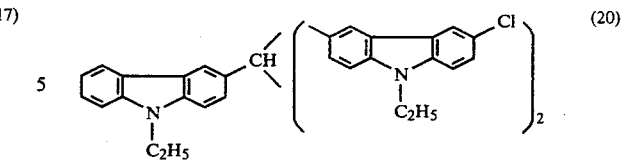 (20)

which melts at 147°–150° C. On silton clay this colour former develops an intense lightfast blue colour with λ max. at 618 nm.

K. 36.6 g of N-methyl-diphenylamine are dissolved in 29.2 g of dimethyl formamide and 50 ml of ethylene chloride. With stirring and cooling, 46 g of phosphoroxy chloride are added to this solution in such a manner that the temperature does not exceed 15° C. The reaction mixture is thereafter stirred for 4 hours at room temperature. Then 14.4 ml of water are added, whereupon the temperature rises rapidly to 50° C. Nitrogen is then introduced and afterwards 75 ml of ethylene chloride and 78 g of N-ethylcarbazole are added. After 5 hours at 65°–70° C. under nitrogen, the reaction mixture is cooled and adjusted to a pH of 7 with 20% sodium hydroxide solution. The ethylene chloride phase is then separated, washed with water and dried over magnesium sulphate. After addition of 100 ml of acetone, the mixture is poured into 2000 ml of methanol and the product precipitates in crystalline form. The crystalline precipitate is collected by filtration and dried in vacuo at 60° C. to give 63.4 g of the compound of the formula (16). The melting point and colour former properties are identical with the particulars given in (F).

EXAMPLE 1

Manufacture of a pressure-sensitive copying paper

A solution of 3 g of the carbazolylmethane compound of formula (15) in 97 g of partially hydrogenated terphenyl is emulsified in a solution of 12 g of pigskin gelatin in 88 g of water of 50° C. A solution of 12 g of gum arabic in 88 g of 50° C. is then added, followed by the addition of 200 ml of water of 50° C. The resultant emulsion is poured into 600 g of ice water and cooled until the temperature is 20° C., in the course of which the coacervation is effected. A sheet of paper is coated with the resultant suspension of microcapsules and dried. A second sheet of paper is coated with silton clay as follows: 25 g of silton clay are suspended in 42 g of water and, with vigorous stirring, the pH is adjusted to 10 with 30% sodium hydroxide solution. After addition of 7.5 g of a binder, for example latex, the suspension is coated on paper and dried. The first sheet and the sheet of paper coated with silton clay are laid on top of each other with the coated sides face to face. Pressure is exerted on the first sheet by writing by hand or with a typewriter and an intense blue copy of excellent lightfastness slowly develops on the sheet coated with silton clay.

If the second sheet is coated with silton clay by adjusting a suspension of 25 g of silton clay and 42 g of water with 30% sodium hydroxide solution to a pH of 5, then 7.5 g of a binder are added, and the suspension is coated on paper, dried, and the procedure is repeated as described above, the colour former of the formula (15) develops its intense lightfast blue colour markedly more quickly.

EXAMPLE 2

Manufacture of a thermoreactive paper 6 g of an aqueous dispersion which contains 1.57% of the carbazolylmethane compound of the formula (15) and 6.7% of polyvinyl alcohol are mixed with 134 g of an aqueous dispersion which contains 14% of 4,4-isopropylidene-diphenol, 8% of attapulgite clay and 6% of polyvinyl alcohol. This mixture is applied to a paper and dried. Contacting the paper with a heated ball-point pen produces an intense blue colour of excellent lightfastness.

Intense and lightfast blue or green colours can also be obtained by using each of the other colour formers of the formulae (11) to (14) and (16) to (20).

I claim:

1. A pressure-sensitive or heat sensitive recording material comprising a carrier and a color forming system containing at least one carbazolylmethane compound of the formula

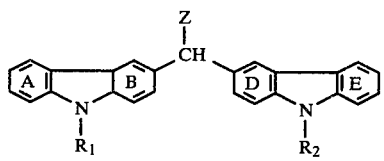

(1)

in which each of $R_1$ and $R_2$ independently represents hydrogen, alkyl of not more than 12 carbon atoms which is unsubstituted or substituted by halogen, hydroxyl, cyano or lower alkoxy, or alkenyl of not more than 12 carbon atoms, acyl of 1 to 12 carbon atoms, phenyl, benzyl, or phenyl or benzyl which is substituted by halogen, lower alkyl, lower alkoxy or nitro, Z represents alkyl of 1 to 12 carbon atoms, alkenyl of not more than 12 carbon atoms, aryl, aralkyl or represents a unsubstituted or substituted heterocyclic radical selected from the group consisting of 3-carbazolyl, N-benzyl-3-carbazolyl, N-lower alkyl-3-carbazolyl, 2-furyl, 2-thienyl, 4-pyridyl, 2-N-methylpyrrolyl, 3-indolyl, 2-lower alkyl-3-indolyl, 2-phenyl-3-indolyl, 1-acetyl-3-indolyl, 1-lower alkyl-2-methyl-3-indolyl, 1-phenyl-3-methyl-5-pyrazolon-4-yl, 1-phenyl-3-methyl-5-amino-pyrazol-4-yl or 1-methyl-2,4-dioxo-quinolin-3-yl, and each of the rings A, B, D and E independently can be substituted by cyano, nitro, halogen, lower alkyl, lower alkoxy or lower alkylcarbonyl.

2. A recording material according to claim 1 in which the carbazolylmethane compound has the formula

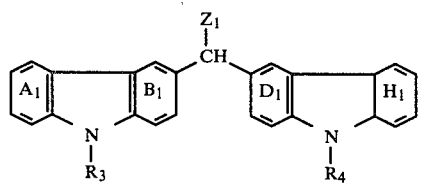

(2)

in which each of $R_3$ and $R_4$ independently represents hydrogen, alkyl of not more than 12 carbon atoms which is unsubstituted or substituted by halogen, cyano or lower alkoxy, phenyl, or benzyl which is unsubstituted or substituted by halogen, lower alkyl or lower alkoxy, and $Z_1$ represents aryl or a heterocyclic radical as defined in claim 1 and each of the rings $A_1$, $B_1$, $D_1$ and $E_1$ independently can be substituted by cyano, halogen, lower alkyl or lower alkoxy.

3. A recording material according to claim 1 in which both carbazolyl radicals in the formula (1) are identical.

4. A recording material according to claim 1 in which the carbazolylmethane compound has the formula

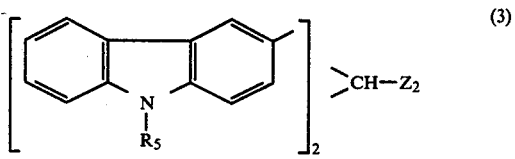

(3)

in which $R_5$ represents alkyl of 1 to 12 carbon atoms, phenyl or benzyl, $Z_2$ represents an aryl radical selected from the group consisting of phenyl, diphenyl and naphthyl, and which can be substituted by halogen, nitro, lower alkyl or lower alkoxy or $Z_2$ represents a heterocyclic radical as defined in claim 1.

5. A recording material according to claim 1 in which the carbazolylmethane compound has the formula

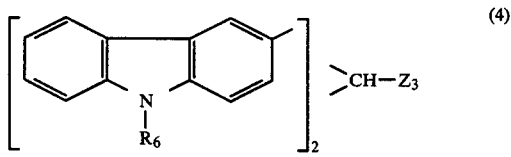

(4)

wherein $R_6$ represents alkyl of 1 to 8 carbon atoms or benzyl, and $Z_3$ represents phenyl or phenyl which is substituted by halogen, lower alkyl, lower alkoxy or the amino group

in which $T_3$ represents lower alkyl, phenyl or lower alkoxyphenyl, and $T_4$ represents hydrogen or lower alkyl.

6. A recording material according to claim 5 which $Z_3$ in formula (4) represents phenyl, halophenyl, methylphenyl, methoxyphenyl, di-(lower alkyl)-aminophenyl, N-phenyl-N-lower alkylaminophenyl, N-methoxyphenyl-N-lower alkylaminophenyl, N-methoxyphenyl-N-lower alkylaminophenyl or N-ethoxyphenyl-N-lower alkylaminophenyl.

7. A recording material according to claim 1 in which the carbazolylmethane compound has the formula

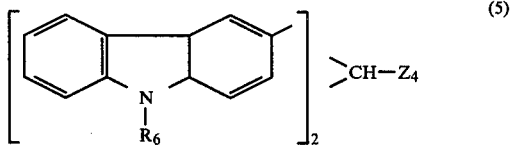

(5)

in which $R_6$ represents alkyl of 1 to 8 carbon atoms or benzyl, and $Z_4$ represents a heterocyclic radical selected from the group consisting of 3-carbazolyl, N-benzyl-3-carbazolyl, N-lower alkyl-3-carbazolyl, 2-furyl, 2-thienyl, 4-pyridyl, 2-N methylpyrrolyl, 3-indolyl, 2-lower alkyl-3-indolyl, 2-phenyl-3-indolyl, 1-acetyl-3-indolyl, 1-lower alkyl-2-methyl-3-indolyl, 1-phenyl-3-methyl-5-pyrazolon-4-yl, 1-phenyl-3-methyl-5-amino-pyrazol-4-yl or 1-methyl-2,4-dioxo-quinolin-3-yl.

8. A recording material according to claim 7 in which $R_6$ represents alkyl of 1 to 8 carbon atoms or benzyl and $Z_4$ represents 3-carbazolyl, N-lower alkyl-3-carbazolyl or N-benzyl-3-carbazolyl.

9. A pressure-sensitive recording material according to claim 1 which contains the carbazolylmethane compound dissolved in an organic solvent, and a solid electron acceptor.

10. A pressure-sensitive recording material according to claim 9 in which the electron acceptor is attapulgite clay, silton clay, a zinc salicylate or a phenol-formaldehyde resin.

11. A pressure-sensitive recording material according to claim 9 in which the carbazolylmethane compound is encapsulated in microcapsules.

12. A thermoreactive recording material according to claim 1 which contains at least one carrier, the carbazolylmethane compound, a solid electron acceptor, and optionally a binder.

13. A process for producing a pressure-sensitive recording material which contains microcapsules containing a colour former and an electron acceptor, in which the colour former is a carbazolylmethane compound of the formula given in claim 1.

* * * * *